United States Patent [19]

Kloek

[11] 4,253,864
[45] Mar. 3, 1981

[54] SUBSTITUTED-1,2,3-THIADIAZOLE-SAFENING AGENTS

[75] Inventor: James A. Kloek, Creve Coeur, Mo.

[73] Assignee: Monsanto Company, St. Louis, Mo.

[21] Appl. No.: 59,717

[22] Filed: Jul. 23, 1979

[51] Int. Cl.$^3$ .................... A01N 25/32; A01N 43/02; A01N 37/18

[52] U.S. Cl. .................... 71/90; 71/118; 71/94

[58] Field of Search .................... 71/90, 118

[56] References Cited

U.S. PATENT DOCUMENTS

| | | | |
|---|---|---|---|
| 3,301,832 | 1/1967 | D'Amico | 71/90 |
| 3,361,752 | 1/1968 | D'Amico | 71/90 |
| 3,547,620 | 12/1970 | Olin | 71/118 |
| 3,654,294 | 4/1972 | Lemieux et al. | 260/302 A |
| 3,734,923 | 5/1973 | Dowding et al. | 71/90 |
| 3,874,873 | 4/1975 | Volpp et al. | 71/90 |
| 3,883,547 | 5/1975 | Schulz et al. | 71/90 |
| 4,115,095 | 9/1978 | Franz et al. | 71/90 |

FOREIGN PATENT DOCUMENTS 2001623  2/1979  United Kingdom .................... 71/90

OTHER PUBLICATIONS

Raap et al., "The section of 1,2,3-Thiadiazoles, etc."; (1967), Can. J. Chem. 46, pp. 1057–1063, (1968).

Primary Examiner—Glennon H. Hollrah
Attorney, Agent, or Firm—Patricia A. Coburn; Donald W. Peterson

[57] ABSTRACT

The invention relates to the safening of crop plants to the use of herbicides utilizing a substituted-1,2,3-thiadiazole or composition containing such compounds to reduce the herbicidal injury to treated crop plants. The invention is also concerned with novel compositions which comprise an acetanilide herbicide and a substituted-1,2,3-thiadiazole.

9 Claims, No Drawings

SUBSTITUTED-1,2,3-THIADIAZOLE-SAFENING AGENTS

This invention relates to the safening of crop plants to the use of herbicides utilizing a safening agent or composition containing a safening agent to reduce the herbicidal injury to treated crop plants. More specifically, the invention is concerned with the methods of treating the plant crop locus with a substituted-1,2,3-thiadiazole or compositions containing such compounds in order to prevent or reduce the injury to the crop plant which would otherwise occur due to the use of an acetanilide herbicide alone. This invention is also concerned with novel compositions which comprise an acetanilide herbicide and a substituted-1,2,3-thiadiazole.

In practice it has been found that acetanilide herbicides are effective in controlling certain weeds in the presence of growing crops. It has been found that when acetanilide herbicides are applied at rates necessary to stunt or kill the weeds, many of these herbicides injure certain crop plants thus slowing growth and development. This injury results in decreased crop yields, thereby reducing the effectiveness of certain herbicides in controlling weeds in the presence of crops. Obviously, a safening agent or composition thereof, that could be used to treat the crop plant locus, resulting in a reduction of injury due to application of the herbicide without a corresponding reduction of herbicidal action on the weed, would be quite beneficial.

1,2,3-Thiadiazole-5-carboxylic acid derivatives of the formula

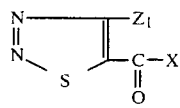

wherein $Z_1$ represents H or an alkyl group optionally interrupted by O and/or S and/or optionally substituted by halogen and X represents $-Y-Z_2$, in which $Z_2$ represents H, an optionally substituted alkyl, aryl or aryl-$C_1$-$C_2$-alkyl group or a monovalent metal equivalent and Y represents O or S, or X represents

in which $Z_3$ and $Z_4$ each represent H, an optionally substituted $C_1$-$C_{18}$-alkyl group, a $C_2$-$C_8$-alkenyl or alkynyl group, an optionally substituted $C_3$-$C_8$-cycloaliphatic hydrocarbon group or an optionally substituted aryl group, or $R_3$ and $R_4$ together with the adjacent nitrogen atom represent a morpholino, piperidino or pyrrolidino group are shown to be herbicidal growth-regulating agents in British Pat. No. 7827354, Publication No. 2,001,623A on Feb. 7, 1979.

In accordance with the novel aspects of the present invention, crop plants can be protected or the tolerance of said crop plants can be increased to minimize injury due to the application thereto of an acetanilide herbicide, without a corresponding reduction in injury to the weeds by treating the crop plant locus with an effective amount of a safening agent comprising a substituted-1,2,3-thiadiazole having the formula

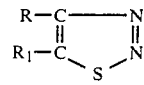

wherein R is selected from the group consisting of lower alkyl, trifluoromethyl, naphthyl, pyridyl, thienyl, phenyl and substituted phenyl containing from one to three substituents individually selected from the class consisting of lower alkyl, lower alkoxy, halogen, nitro and trifluoromethyl; and $R_1$ is selected from the group consisting of hydrogen, halogen, phenyl and a

group wherein $R_2$ is lower alkoxy or phenylamino; provided that when $R_2$ is lower alkoxy, R is not lower alkyl or phenyl and further provided that when R is 3-methoxyphenyl, $R_1$ is not hydrogen.

It is preferred that the substituted phenyl radicals represented by R contain one or two substituents.

The class of acetanilide herbicides employed in the compositions and methods of this invention include 2-chloro-2',6'-diethyl-N-(methoxymethyl)acetanilide, 2-chloro-2',6'-diethyl-N-(butoxymethyl)acetanilide, 2-chloro-N-(2-methoxy-1-methylethyl)-6'-ethyl-o-acetotoluidide and the like. The preparation and use of 2-chloro-2',6'-diethyl-N-(methoxymethyl)acetanilide and 2-chloro-2',6'-diethyl-N-(butoxymethyl)acetanilide to control the growth of undesired plants is described in U.S. Pat. No. 3,442,945. Herbicidal compositions containing these compounds are disclosed in U.S. Pat. No. 3,547,620. U.S. Pat. No. 3,937,730 discloses 2-chloro-N-(2-methoxy-1-methylethyl)-6'-ethyl-o-acetotoluidide.

Treatment of the crop plant locus refers to the application of the herbicide and safening agent, in admixture or in sequence, to the plant growth medium as well as directly to the plants or to parts thereof such as roots, stems, leaves, flowers, fruits or other plant parts. Also included in the term is treatment of plant seeds prior to planting with a safening agent.

As employed herein, the term "lower alkyl" designates alkyl radicals which have up to four carbon atoms in a straight or branched chain, such as, for example, methyl, ethyl, propyl, isopropyl, butyl, isobutyl, sec-butyl and t-butyl.

The term "halogen" as used herein includes chloro, bromo, fluoro and iodo.

Illustrative of the substituted phenyl groups which R represents are mono-substituted phenyl wherein the substituent is in the ortho, meta or para position, for example, methylphenyl, butylphenyl, methoxyphenyl, butoxyphenyl, fluorophenyl, chlorophenyl, bromophenyl, iodophenyl, trifluoromethylphenyl, nitrophenyl and the like and the di- and tri-substituted phenyl groups wherein the substituents are the same or different and are located in the 2,3,4,5 or 6 positions of the phenyl ring, for example, dichlorophenyl, difluorophenyl, methylchlorophenyl, butoxy fluorophenyl, (methyl)(butyl)phenyl, (methoxy)(butoxy)phenyl, dimethoxyphenyl, methyl nitrophenyl, trichlorophenyl, trimethylphenyl, tributoxyphenyl and the like.

As employed herein, the term "lower alkoxy" designates alkoxy radicals which have up to four carbon atoms in a straight or branched chain, such as, for example, ple, methoxy, ethoxy, propoxy, isopropoxy, butoxy, isobutoxy, sec-butoxy and t-butoxy.

The safening agents of this invention may be applied in a mixture with the above-named herbicides, or the components of the mixture can be used sequentially. In the case of a sequential treatment, the safening agent may be applied either before or after application of the herbicide. Effective herbicidal amounts of the particular herbicide employed are well understood by those skilled in the art, and such amounts are used together with an effective safening amount of a substituted-1,2,3-thiadiazole. The term "effective safening amount" refers to the amount of safening agent required to effectively reduce the crop injury caused by application of a herbicide at a given rate. The amount of safening agent employed in the method and compositions of this invention will vary depending upon the particular herbicide with which the safening agent is employed, the rate of application of the herbicide, the crop to be protected as well as the manner of application of the safening agent. The ratio of herbicide to safening agent may vary depending upon the age of the plants at time of treatment, climatic conditions, soil, etc. Ratios of from 1:16 to 16:1 are shown to be effective in the tests below. However, it is generally preferred to employ a weight ratio of herbicide to safening agent ranging from about 1:8 to 8:1.

In each test a crop plant, with or without weeds, is grown in a container, and there is an application of the herbicide and a safening agent. In each test there is also a container which receives no application at all, a container to which only the herbicide is applied, and a container to which only the safening agent is applied. The untreated container shows normal plant growth as standard, and it also serves as an indicator of extraneous conditions which may affect the plants. The other containers show the effect of the herbicide alone, the effect of the safening agent alone, and the effect of the application of both. These effects are in terms of percent inhibition of plant growth relative to the plants in the untreated container.

The "safening effect" is determined by adding the percent inhibition obtained when the herbicide is applied alone to the percent inhibition obtained when the safening agent is applied alone (in no instance, however, will this sum be taken as greater than 100), then subtracting from that sum the percent inhibition obtained when the herbicide and safening agent are both applied. The percent inhibition as used hereinafter refers to the percent of weeds or crop plants which are injured or killed.

The effectiveness of the substituted-1,2,3-thiadiazoles for the purposes of this invention is demonstrated by the results obtained using the various test procedures hereinafter described. Specific individual compounds employed as safening agents in these procedures are identified by the compound number given in Table XII. The herbicide as used in the test procedures was in the form of a formulation comprising the named active ingredient, a solvent and an emulsifier. All rates of application of the herbicide and safening agent in the following examples are shown in kilograms per hectare unless otherwise noted. An asterick indicates a safening effect of 0 to 19%. In those tests where the procedures are replicated, the results represent an average of all replicates. The compounds as employed in the following examples serve only to illustrate the novel aspects of the invention and should not be construed as a limitation on its scope.

EXAMPLE 1

A good grade of top soil was placed in a container and compacted to a depth of approximately 1.27 cm. from the top of said container. A predetermined number of seeds of each of the crop species to be tested were placed on top of the soil. A quantity of soil sufficient to substantially fill the container was measured and placed in a second container. A measured quantity of the safening agent dispersed or dissolved in a suitable carrier was applied to the soil in the second container. A measured quantity of formulated 2-chloro-2',6'-diethyl-N-(methoxymethyl)acetanilide dispersed or dissolved in a suitable carrier was then sprayed on the soil previously treated with the safening agent. The soil containing the safening agent and herbicide was thoroughly mixed. This mixing is sometimes referred to as incorporation of the herbicide and safening agent into the soil. The mixing or incorporation provides a substantially uniform distibution of the safening agent and herbicide throughout the soil. The seeds were covered with the soil containing the safening agent and herbicide and the pots were leveled. The pots were then placed on a sand bench in the greenhouse and watered from below as needed. The plants were observed at the end of approximately 21 days and the results in terms of percent inhibition of each seed lot were recorded.

The test results in Table I illustrate the reduction in the inhibition of crop plants which was achieved when 2-chloro-2',6'-diethyl-N-(methoxymethyl)acetanilide was used in conjunction with a safening agent of this invention.

TABLE I

| Safening Agent | Safening Agent Rate | Herbicide Rate | Safening Effect | | |
|---|---|---|---|---|---|
| | | | Rice | Sorghum | Wheat |
| (1) | 8.96 | 2.24 | * | * | * |
| (2) | 8.96 | 2.24 | * | 25 | * |
| (3) | 8.96 | 2.24 | * | * | * |
| (4) | 8.96 | 2.24 | * | 21 | * |
| (5) | 8.96 | 4.48 | * | * | * |
| (6) | 8,96 | 2.24 | * | 35 | * |
| (7) | 8.96 | 4.48 | 25 | * | * |
| (8) | 8.96 | 2.24 | 20 | * | 25 |
| (9) | 8.96 | 4.48 | * | * | * |
| (10) | 8.96 | 4.48 | * | 20 | * |
| (11) | 8.96 | 4.48 | * | * | * |
| (12) | 8.96 | 2.24 | * | * | * |
| (13) | 8.96 | 4.48 | * | * | * |
| (14) | 8.96 | 4.48 | * | 30 | 60 |
| (15) | 8.96 | 4.48 | * | * | * |
| (16) | 8.96 | 2.24 | 23 | 50 | 65 |
| (17) | 8.96 | 2.24 | * | 20 | 35 |
| (18) | 8.96 | 4.48 | * | * | * |
| (19) | 8.96 | 2.24 | * | * | * |
| (20) | 8.96 | 4.48 | * | * | * |
| (21) | 8.96 | 4.48 | * | 45 | * |
| (22) | 8.96 | 2.24 | * | 28 | * |
| (23) | 8.96 | 2.24 | * | * | * |

EXAMPLE 2

The procedure of Example 1 was employed. The test results in Table II illustrate the reduction in the inhibition of crop plants which was achieved when 2-chloro-2',6'-diethyl-N-(methoxymethyl)acetanilide at various application rates was used in conjunction with a safening agent of this invention.

TABLE II

| Safening Agent | Safening Agent Rate | Herbicide Rate | Safening Effect | | |
|---|---|---|---|---|---|
| | | | Rice | Sorghum | Wheat |
| (2) | 8.96 | 0.56 | * | 35 | * |
| | 8.96 | 1.12 | * | 65 | * |
| | 8.96 | 2.24 | 30 | 60 | * |
| | 8.96 | 4.48 | * | 38 | * |
| (10) | 8.96 | 0.56 | * | 35 | * |
| | 8.96 | 1.12 | * | 30 | * |
| | 8.96 | 2.24 | * | * | * |
| | 8.96 | 4.48 | * | * | * |
| (14) | 8.96 | 0.56 | * | 55 | 40 |
| | 8.96 | 1.12 | * | 60 | 30 |
| | 8.96 | 2.24 | * | 60 | * |
| | 8.96 | 4.48 | * | 70 | * |

EXAMPLE 3

The procedure of Example 1 was employed utilizing 2-chloro-2',6'-diethyl-N-(butoxymethyl)acetanilide as the herbicide.

The test results in Table III illustrate the reduction in the inhibition of crop plants which was achieved when 2-chloro-2',6'-diethyl-N-(butoxymethyl)acetanilide was used in conjunction with a safening agent of this invention.

TABLE III

| Safening Agent | Safening Agent Rate | Herbicide Rate | Safening Effect | | |
|---|---|---|---|---|---|
| | | | Rice | Sorghum | Wheat |
| (1) | 8.96 | 4.48 | * | * | 35 |
| (2) | 8.96 | 6.72 | * | 30 | * |
| (3) | 8.96 | 6.72 | * | 30 | * |
| (4) | 8.96 | 6.72 | * | * | * |
| (5) | 8.96 | 6.72 | 20 | * | * |
| (6) | 8.96 | 6.72 | * | 30 | 25 |
| (7) | 8.96 | 6.72 | 40 | 32 | 55 |
| (8) | 8.96 | 6.72 | * | * | * |
| (9) | 8.96 | 6.72 | 50 | * | 25 |
| (10) | 8.96 | 6.72 | * | * | * |
| (11) | 8.96 | 6.72 | * | 30 | 40 |
| (12) | 8.96 | 4.48 | 20 | 22 | 27 |
| (13) | 8.96 | 6.72 | * | * | 40 |
| (14) | 8.96 | 6.72 | * | * | 35 |
| (15) | 8.96 | 6.72 | 40 | * | * |
| (16) | 8.96 | 6.72 | * | * | * |
| (17) | 8.96 | 6.72 | * | * | * |
| (18) | 8.96 | 6.72 | * | 20 | * |
| (19) | 8.96 | 6.72 | * | * | 25 |
| (20) | 8.96 | 6.72 | 20 | * | * |
| (21) | 8.96 | 6.72 | 25 | * | 50 |
| (22) | 8.96 | 6.72 | * | 20 | * |
| (23) | 8.96 | 4.48 | 55 | 60 | 60 |

As noted previously, the substituted-1,2,3-thiadiazoles may be used to protect crops from herbicidal injury without a corresponding diminution in the high level of weed control demonstrated by the herbicides. Examples 4 and 5 are illustrative of such activity.

EXAMPLE 4

A good grade of top soil was placed in a container and compared to a depth of approximately 1.27 cm. from the top of said container. A predetermined number of sorghum, wheat and green foxtail seeds were placed on top of the soil. A quantity of soil sufficient to substantially fill the container was measured and placed in a second container. A measured quantity of the safening agent dispersed or dissolved in a suitable carrier was applied to the soil in the second container. A measured quantity of formulated 2-chloro-2',6'-diethyl-N-(methoxymethyl)acetanilide dispersed or dissolved in a suitable carrier was then sprayed on the soil previously treated with the safening agent. The soil containing the safening agent and herbicide was thoroughly mixed. This mixing is sometimes referred to as incorporation of the herbicide and safening agent into the soil. The mixing or incorporation provides a substantially uniform distribution of the safening agent and herbicide throughout the soil. The seeds were covered with the soil containing the safening agent and herbicide and the pots were leveled. The pots were then placed on a sand bench in the greenhouse and watered from below as needed. The plants were observed at the end of approximately 21 days and the results in terms percent inhibition of each seed lot were recorded.

Tables IV-IX summarize the results of six separate tests which illustrate the reduction in the inhibition of crop plants without a corresponding diminution in weed control which was achieved when 2-chloro-2',6'-diethyl-N-(methoxymethyl)acetanilide was used in conjunction with a safening agent of this invention.

TABLE IV

| Safening Agent | Safening Agent Rate | Herbicide Rate | Percent Inhibition | | |
|---|---|---|---|---|---|
| | | | Sorghum | Wheat | Green Foxtail |
| | — | 0.56 | 80 | 40 | 98 |
| | — | 1.12 | 85 | 50 | 99 |
| | — | 2.24 | 90 | 60 | 100 |
| | — | 4.48 | 98 | 70 | 100 |
| (4) | 8.96 | — | 0 | 0 | 0 |
| | 8.96 | 0.56 | 20 | 20 | 99 |
| | 8.96 | 1.12 | 40 | 40 | 99 |
| | 8.96 | 2.24 | 90 | 40 | 100 |
| | 8.96 | 4.48 | 90 | 80 | 100 |

TABLE V

| Safening Agent | Safening Agent Rate | Herbicide Rate | Percent Inhibition | | |
|---|---|---|---|---|---|
| | | | Sorghum | Wheat | Green Foxtail |
| | — | 0.56 | 60 | 40 | 95 |
| | — | 1.12 | 70 | 60 | 99 |
| | — | 2.24 | 80 | 70 | 99 |
| | — | 4.48 | 95 | 90 | 100 |
| (6) | 8.96 | — | 0 | 0 | 50 |
| | 8.96 | 0.56 | 20 | 30 | 100 |
| | 8.96 | 1.12 | 30 | 70 | 100 |
| | 8.96 | 2.24 | 60 | 75 | 100 |
| | 8.96 | 4.48 | 70 | 100 | 100 |

TABLE VI

| Safening Agent | Safening Agent Rate | Herbicide Rate | Percent Inhibition | | |
|---|---|---|---|---|---|
| | | | Sorghum | Wheat | Green Foxtail |
| | — | 0.56 | 8 | 25 | 90 |
| | — | 1.12 | 40 | 30 | 90 |
| | — | 2.24 | 53 | 33 | 97 |
| | — | 4.48 | 55 | 48 | 99 |
| (16) | 8.96 | — | 0 | 0 | 0 |
| | 8.96 | 0.56 | 0 | 20 | 100 |
| | 8.96 | 1.12 | 15 | 0 | 100 |
| | 8.96 | 2.24 | 35 | 0 | 99 |
| | 8.96 | 4.48 | 70 | 0 | 100 |
| (23) | 8.96 | — | 0 | 0 | 0 |
| | 8.96 | 0.56 | 0 | 0 | 98 |
| | 8.96 | 1.12 | 15 | 10 | 100 |
| | 8.96 | 2.24 | 10 | 25 | 100 |
| | 8.96 | 4.48 | 85 | 40 | 99 |

TABLE VII

| Safening Agent | Safening Agent Rate | Herbicide Rate | Percent Inhibition Sorghum | Wheat | Green Foxtail |
|---|---|---|---|---|---|
|  | — | 0.56 | 40 | 40 | 98 |
|  | — | 1.12 | 60 | 50 | 99 |
|  | — | 2.24 | 80 | 60 | 100 |
|  | — | 4.48 | 100 | 75 | 100 |
| (17) | 8.96 | — | 0 | 0 | 0 |
|  | 8.96 | 0.56 | 50 | 30 | 100 |
|  | 8.96 | 1.12 | 40 | 30 | 99 |
|  | 8.96 | 2.24 | 60 | 40 | 100 |
|  | 8.96 | 4.48 | 75 | 40 | 100 |

TABLE VIII

| Safening Agent | Safening Agent Rate | Herbicide Rate | Percent Inhibition Sorghum | Wheat | Green Foxtail |
|---|---|---|---|---|---|
|  | — | 0.56 | 70 | 50 | 80 |
|  | — | 1.12 | 75 | 65 | 98 |
|  | — | 2.24 | 88 | 75 | 98 |
|  | — | 4.48 | 90 | 75 | 99 |
| (21) | 8.96 | — | 0 | 0 | 0 |
|  | 8.96 | 0.56 | 10 | 0 | 90 |
|  | 8.96 | 1.12 | 15 | 20 | 98 |
|  | 8.92 | 2.24 | 20 | 20 | 98 |
|  | 8.96 | 4.48 | 30 | 50 | 99 |

TABLE IX

| Safening Agent | Safening Agent Rate | Herbicide Rate | Percent Inhibition Sorghum | Wheat | Green Foxtail |
|---|---|---|---|---|---|
|  | — | 0.56 | 60 | 55 | 99 |
|  | — | 1.12 | 80 | 70 | 100 |
|  | — | 2.24 | 90 | 85 | 100 |
|  | — | 4.48 | 99 | 98 | 100 |
| (22) | 8.96 | — | 0 | 0 | 0 |
|  | 8.96 | 0.56 | 30 | 30 | 98 |
|  | 8.96 | 1.12 | 50 | 70 | 100 |
|  | 8.96 | 2.24 | 60 | 90 | 100 |
|  | 8.96 | 4.48 | 80 | 95 | 100 |

EXAMPLE 5

A good grade of top soil was placed in a plastic pot and compacted to a depth of approximately 1.27 cm. from the top of said pot. A predetermined number of wheat, green foxtail, downy brome and wild oats seeds were placed on top of the soil. A soil cover layer, approximately 1.27 cm. deep, was placed on top of said seeds. The soil was then treated with a mixture comprising a safening agent and a formulated 2-chloro-2',6'-diethyl-N-(methoxymethyl)acetanilide dispersed or dissolved in a suitable solvent. The pots were given overhead water and subirrigated as required for the duration of the test. The percent inhibition was observed approximately 21 days after treatment.

Table X summarizes the results of the tests conducted in accordance with this procedure.

TABLE X

| Safening Agent | Safening Agent Rate | Herbicide Rate | Percent Inhibition Wheat | Green Foxtail | Downy Brome | Wild Oats |
|---|---|---|---|---|---|---|
|  |  | 0.14 | 45 | 80 | 85 | 60 |
|  |  | 0.56 | 83 | 97 | 94 | 88 |
|  |  | 2.24 | 92 | 99 | 100 | 98 |
| (21) | 0.14 | — | 0 | 0 | 0 | 0 |
|  | 0.14 | 0.14 | 40 | 92 | 80 | 40 |
|  | 0.14 | 0.56 | 83 | 100 | 99 | 90 |
|  | 0.14 | 2.24 | 98 | 98 | 99 | 98 |
|  | 0.56 | — | 0 | 0 | 0 | 0 |
|  | 0.56 | 0.14 | 53 | 94 | 75 | 55 |
|  | 0.56 | 0.56 | 65 | 94 | 88 | 85 |
|  | 0.56 | 2.24 | 93 | 99 | 99 | 97 |
|  | 2.24 | — | 0 | 0 | 0 | 0 |
|  | 2.24 | 0.14 | 20 | 73 | 70 | 40 |
|  | 2.24 | 0.56 | 75 | 97 | 90 | 85 |
|  | 2.24 | 2.24 | 88 | 100 | 99 | 97 |

As noted above, crop plants may be protected from herbicidal injury by treating the crop seed with the safening agent prior to planting. Example 6 illustrates such activity.

EXAMPLE 6

Sorghum seeds were treated with a solution of the appropriate safening agent dissolved in dichloromethane. The solvent was removed by evaporation leaving a coating of the safening agent on the seed. Untreated and treated sorghum seeds were planted in pots. Selected weed species were planted in separate pots. A 1.27 cm. deep soil cover layer was placed on the pre-seeded pots. The soil surface was then treated with formulated 2-chloro-2',6'-diethyl-N-(methoxymethyl)acetanilide.

The pots were given overhead water and subirrigated as required for the duration of the test. Approximately 21 days later, the results were observed and recorded.

The results in Table IX show that seed treatment with a safening agent will serve to reduce the inhibition of sorghum plants upon application of 2-chloro-2',6'-diethyl-N-(methoxymethyl)acetanilide while maintaining a high level of weed control. The application rate for the safening agent is given in terms of percent weight of safening agent relative to seed weight. The application rate of the herbicide is given in kilograms per hectare.

TABLE XI

| Safening Agent | Safening Agent Rate | Herbicide Rate | Percent Inhibition Sorghum |
|---|---|---|---|
|  | — | 0.14 | 60 |
|  | — | 1.12 | 93 |
|  | — | 4.48 | 99 |
| (14) | 0.04 | — | 5 |
|  | 0.04 | 0.14 | 38 |
|  | 0.04 | 1.12 | 68 |
|  | 0.04 | 4.48 | 97 |
|  | 0.14 | — | 5 |
|  | 0.14 | 0.14 | 15 |
|  | 0.14 | 1.12 | 20 |
|  | 0.14 | 4.48 | 63 |
|  | 1.12 | — | 100 |
|  | 1.12 | 0.14 | 90 |
|  | 1.12 | 1.12 | 88 |
|  | 1.12 | 4.48 | 98 |

| Herbicide Rate | Percent Inhibition | | | | | | |
|---|---|---|---|---|---|---|---|
|  | Smartweed | Lambsquarter | Green Foxtail | Crabgrass | Panicum | Barnyard Grass | Sorghum |
| 0.14 | 0 | 63 | 90 | 90 | 100 | 99 | 25 |
| 0.28 | 63 | 75 | 99 | 99 | 100 | 100 | 80 |
| 1.12 | 93 | 88 | 100 | 99 | 100 | 100 | 88 |
| 4.48 | 100 | 100 | 100 | 100 | 100 | 100 | 99 |

Most of the preceding examples show the use of the described test procedures with more than one safening agent of this invention. It should be understood that all of the tests within a single example were not necessarily conducted at the same time. It should also be understood, that an untreated container, plus containers with the herbicide alone and the safening agent alone, are employed for each test initiation rate as controls to obtain the herbicide and safening effect data for tests begun on that particular date.

The above examples illustrate that while the substituted-1,2,3-thiadiazoles of the present invention generally safen crop plants, especially rice, sorghum and wheat crops to the herbicidal effects of acetanilide herbicides, those skilled in the art will appreciate that the compounds of the invention may be used most effectively in safening sorghum and wheat against injury due to the herbicidal effects of 2-chloro-2',6'-diethyl-N-(methoxymethyl)acetanilide and rice against injury due to the herbicidal effects of 2-chloro-2',6'-diethyl-N-(butoxymethyl)acetanilide.

The herbicide, safening agent or mixture thereof may be applied to the plant locus alone or the herbicide, safening agent or mixture thereof may be applied in conjunction with a material referred to in the art as an adjuvant in liquid or solid form. Mixtures containing the appropriate herbicide and safening agent usually are prepared by admixing said herbicide and safening agent with an adjuvant including diluents, extenders, carriers and conditioning agents to provide compositions in the form of finely-divided particulate solids, granules, pellets, wettable powders, dusts, solutions and aqueous dispersions or emulsions. Thus, the mixture may include an adjuvant such as a finely-divided particulate solid, a solvent liquid of organic origin, water, a wetting agent, dispersing agent, or emulsifying agent or any suitable combination of these.

When applying the herbicide, safening agent or mixture thereof to the plant locus useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful include for example, Stoddard solvent, acetone, alcohols, glycols, ethyl acetate, benzene and the like. Such compositions, particularly liquids and wettable powders, usually contain as a conditioning agent one or more surface-active agents in amounts sufficient to render a given composition readily dispersible in water or in oil. By the term "surface-active agent", it is understood that wetting agents, dispersing agents, suspending agents and emulsifying agents are included therein. Such surface-active agents are well known and reference is made to U.S. Pat. No. 2,547,724, columns 3 and 4, for detailed examples of the same.

Compositions of this invention generally contain from about 5 to 95 parts herbicide and safening agent, about 1 to 50 parts surface-active agent and about 4 to 94 parts solvent, all parts being by weight based on the total weight of the composition.

The application of the herbicide, safening agent or mixture thereof in a liquid or particulate solid form can be carried out by conventional techniques utilizing, for example, spreaders, power dusters, boom and hand sprayers, spray dusters and granular applications. The compositions can also be applied from airplanes as a dust or spray. If desired, application of the compositions of the invention to plants can be accomplished by incorporating the compositions in the soil or other media.

The above examples also illustrate that the crop may be protected by treating the crop seed with an effective amount of safening agent prior to planting. Generally, small amounts of safening agent are required to treat such seeds. Example 6 illustrates that a weight ratio of as little as 0.6 parts of safener per 1000 parts of seed may be effective. The amount of safener utilized in treating the seed may be increased if desired. Generally, however, a weight ratio of safening agent to seed weight may range from 0.1 to 10.0 parts of safening agent per 1000 parts of seed. The determination of the effective amount of safening agent required is well within the skill of the art.

Since only a very small amount of active safening agent is usually required for the seed treatment, the safening agent preferably is formulated as a powder or an emulsifiable concentrate which can be diluted with water by the seed treater for use in the seed treating apparatus. Of course, under certain conditions, it may be desirable to dissolve the safening agent in an organic solvent for use as a seed treatment or the pure compound alone may be used under properly controlled conditions.

There are thus also provided by this invention novel seed treating compositions containing one or more of the described active safening agents intimately dispersed in an inert carrier or diluent for the intended use. Such carriers may be either solids, such as talc, clay, diatomaceous earth, sawdust, calcium carbonate, and the like or liquids such as water, kerosene, acetone, benzene, toluene, xylene, and the like in which the active agent may be either dissolved or dispersed. Emulsifying agents are advisably used to achieve a suitable emulsion if two immiscible liquids are used as a carrier. Wetting agents may also be used to aid in dispersing the active safening agent in liquids used as a carrier in which the agent is not completely soluble. Emulsifying agents and wetting agents are sold under numerous tradenames and may be either pure compounds, mixtures of compounds of the same general groups, or they may be mixtures of compounds of different classes. Typical satisfactory surface-active agents which may be used are alkali metal, higher alkylarylsulfonates such as sodium dodecylbenzenesulfonate and the sodium salts of alkylnaphthalenesulfonic acids, fatty alcohol sulfates such as the sodium salts of monoesters of sulfuric acid with n-aliphatic alcohols containing 8–18 carbon atoms, long chain quaternary ammonium compounds, sodium salts of petroleum-derived alkylammonium compounds, sodium salts of petroleum-derived alkylsulfonic acids, polyethylene sorbitan monooleate, alkylaryl polyether alcohols, water-soluble lignin sulfonate salts, alkalicasein compositions, long chain alcohols usually containing 10–18 carbon atoms, and condensation products of ethylene oxide with fatty acids, alkylphenols and mercaptans.

The substituted 1,2,3-thiadiazoles employed in the methods of the present invention may be prepared in accordance with known procedures such as disclosed by U.S. Pat. No. 3,654,294 and the above-identified British Pat. No. 2,001,623A.

In accordance with the above known procedure, the following compounds found in Table XII have been prepared.

TABLE XII

| Compound Number | Compound | Physical Constant m.p. °C. | Physical Constant b.p. °C. |
|---|---|---|---|
| (1) | 4-phenyl-1,2,3-thiadiazole | 76–78 | — |
| (2) | 4-phenyl-5-chloro-1,2,3-thiadiazole | 85–88 | — |
| (3) | N-4-diphenyl-1,2,3-thiadiazole-5-carboxamide | 82–85 | — |
| (4) | 4-(4-methylphenyl)-1,2,3-thiadiazole | 68–70 | — |
| (5) | 4-(4-methoxyphenyl)-1,2,3-thiadiazole | 89–93 | — |
| (6) | 4-(3-bromophenyl)-1,2,3-thiadiazole | 118–120 | — |
| (7) | 4-(4-fluorophenyl)-1,2,3-thiadiazole | 96.5–98.5 | — |
| (8) | 4-(4-fluorophenyl)-5-chloro-1,2,3-thiadiazole | 108–110 | — |
| (9) | 4-(4-chlorophenyl)-1,2,3-thiadiazole | 135–138 | — |
| (10) | 4-(3-chlorophenyl)-1,2,3-thiadiazole | 81–84 | — |
| (11) | 4-(2-chlorophenyl)-1,2,3-thiadiazole | — | 110 @ 0.15 mm Hg |
| (12) | 4-(2,4-dichlorophenyl)-1,2,3-thiadiazole | 107–110 | — |
| (13) | 4-(2,5-dichlorophenyl)-1,2,3-thiadiazole | 65–68 | — |
| (14) | 4-[3-(trifluoromethyl)phenyl]-1,2,3-thiadiazole | 40–42 | — |
| (15) | 4-[4-(trifluoromethyl)phenyl]-1,2,3-thiadiazole | 88–92 | — |
| (16) | 4-[2-(trifluoromethyl)phenyl]-1,2,3-thiadiazole | — | 90–100 @ 0.4 mm Hg |
| (17) | 4-[2-chloro-5-(trifluoromethyl)phenyl]-1,23-thiadiazole | 68–71 | — |
| (18) | 4-(3-nitrophenyl)-1,2,3-thiadiazole | 141–143 | — |
| (19) | 4-(2-naphthalenyl)-1,2,3-thiadiazole | 113 | — |
| (20) | 3-(1,2,3-thiadiazol-4-yl) pyridine | 85–89 | — |
| (21) | 4-(2-thienyl)-1,2,3-thiadiazole | 61–63 | — |
| (22) | 4-methyl-5-phenyl-1,2,3-thiadiazole | — | 90–95 @ 0.15 mm Hg |
| (23) | 4-(trifluoromethyl)-1,2,3-thiadiazole-5-carboxylic acid ethyl ester | — | 65 @0.4 mm Hg |

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A composition comprising a herbicidally effective amount of 2-chloro-2',6'-diethyl-N-(methoxymethyl)acetanilide and an effective safening amount of a compound selected from the group consisting of:
4-(4-methylphenyl)-1,2,3-thiadiazole;
4-(3-bromophenyl)-1,2,3-thiadiazole;
4-(3-chlorophenyl)-1,2,3-thiadiazole;
4-[3-(trifluoromethyl)phenyl]-1,2,3-thiadiazole;
4-[2-(trifluoromethyl)phenyl]-1,2,3-thiadiazole;
4-[2-chloro-5-(trifluoromethyl)phenyl]-1,2,3-thiadiazole.

2. A composition according to claim 1 wherein said compound is 4-[3-(trifluoromethyl)phenyl]-1,2,3-thiadiazole.

3. A composition according to claim 1 wherein said compound is 4-[2-(trifluoromethyl)phenyl]-1,2,3-thiadiazole.

4. A method for reducing herbicidal injury to sorghum crop plants which comprises treating the plant locus with a herbicidally effective amount of 2-chloro-2',6'-diethyl-N-(methoxymethyl)acetanilide and an effective safening amount of a compound selected from the group consisting of:
4-(4-methylphenyl)-1,2,3-thiadiazole;
4-(3-bromophenyl)-1,2,3-thiadiazole;
4-(3-chlorophenyl)-1,2,3-thiadiazole;
4-[3-(trifluoromethyl)phenyl]-1,2,3-thiadiazole;
4-[2-(trifluoromethyl)phenyl]-1,2,3-thiadiazole;
4-[2-chloro-5-(trifluoromethyl)phenyl]-1,2,3-thiadiazole.

5. A method according to claim 4 wherein said compound is 4-[3-(trifluoromethyl)phenyl]-1,2,3-thiadiazole.

6. A method according to claim 5 wherein said compound is 4-[2-(trifluoromethyl)phenyl]-1,2,3-thiadiazole.

7. A method for reducing herbicidal injury to wheat crop plants which comprises treating the plant locus with a herbicidally effective amount of 2-chloro-2',6'-diethyl-N-(methoxymethyl)acetanilide and an effective safening amount of a compound selected from the groups consisting of:
4-[3-(trifluoromethyl)phenyl]-1,2,3-thiadiazole;
4-[2-(trifluoromethyl)phenyl]-1,2,3-thiadiazole;
4-[2-chloro-5-(trifluoromethyl)phenyl]-1,2,3-thiadiazole;
4-(4-methylphenyl)-1,2,3-thiadiazole.

8. A method according to claim 7 wherein said compound is 4-[3-(trifluoromethyl)phenyl]-1,2,3-thiadiazole.

9. A method according to claim 7 wherein said compound is 4-[2-(trifluoromethyl)phenyl]-1,2,3-thiadiazole.

* * * * *